(12) United States Patent
Charne et al.

(10) Patent No.: US 6,914,171 B2
(45) Date of Patent: Jul. 5, 2005

(54) BRASSICA NAPUS WITH EARLY MATURITY (EARLY NAPUS) AND RESISTANCE TO AN AHAS-INHIBITOR HERBICIDE

(75) Inventors: David G. Charne, Guelph (CA); Jayantilal D. Patel, Thornhill (CA); Alan Grombacher, Beaumont (CA)

(73) Assignee: Pioneer Hi-Bred International Inc., Johnston, IA (US)

( * ) Notice: Subject to any disclaimer, the term of this patent is extended or adjusted under 35 U.S.C. 154(b) by 95 days.

(21) Appl. No.: 09/994,092

(22) Filed: Nov. 16, 2001

(65) Prior Publication Data

US 2002/0120962 A1 Aug. 29, 2002

(30) Foreign Application Priority Data

Nov. 17, 2000 (CA) .............................. 2326283

(51) Int. Cl.$^7$ .......................... A01H 1/00; A01H 5/00; A01H 5/10
(52) U.S. Cl. ...................... 800/306; 435/418; 800/266; 800/298; 800/300
(58) Field of Search ............................... 435/410, 418; 800/306, 260, 298, 300, 266

(56) References Cited

U.S. PATENT DOCUMENTS

| | | | | |
|---|---|---|---|---|
| 5,304,719 A | * | 4/1994 | Segebart | 800/303 |
| 5,367,109 A | * | 11/1994 | Segebart | 800/320.1 |
| 5,387,758 A | | 2/1995 | Wong et al. | 800/230 |
| 5,545,821 A | | 8/1996 | Wong et al. | 800/230 |
| 5,763,755 A | * | 6/1998 | Carlone | 800/320.1 |
| 5,767,366 A | | 6/1998 | Sathasivan et al. | 800/300 |
| 5,773,702 A | | 6/1998 | Penner et al. | 800/230 |
| 5,850,009 A | * | 12/1998 | Kevern | 800/271 |
| 6,222,101 B1 | * | 4/2001 | Patel | 800/306 |
| 6,303,849 B1 | | 10/2001 | Potts et al. | 800/306 |

OTHER PUBLICATIONS

Osborn et al 1997, Genetics 146:1123–1129.*
Miki, et al., 1990, *Theoretical and Applied Genetics*, 80:449–458, "Transformation of *Brassica napus* canola cultivars with *Arabidopsis thaliana* acetohydroxyacid synthase genes and analysis of herbicide resistence".
Swanson, et al., 1988, *Plant Cell Reports*, 7:83–87, "The characterization of herbicide tolerant plants in *Brassica napus* L. after *in vitro* selection of microspores and protoplasts".
Rutledge, et al., 1991, *Mol. Gen. Genet.*, 229:31–40, "Molecular characterization and genetic origin of the *Brassica napus* acetohydroxyacid synthase multigene family".
Ouellet, et al., 1992, *Plant Journal*, 2:321–330, "Members of the acetohydroxyacid synthase multigene family of *Brassica napus* have divergent patterns of expression".

Hattori, et al., 1992, *Can. J. Bot.*, 70: 1957–1963, "DNA sequence relationships and origins of acetohydroxy acid synthase genes of *Brassica napus*".
Swanson, et al., 1989, *Theor. Appl. Genet.*, 78:525–530, "Microspore mutagenesis and selection: Canola plants with field tolerance to imidazolinones".
Newhouse, et al., 1992, *Plant Physiol.*, 100:882–886, "Tolerance to imidazolinone herbicides in wheat".
Sprague, et al., 1997, *Weed Technology*, 11:241–247, "Common cocklebur (*Xanthium strumarium*) resistance to selected ALS–inhibiting herbicides".
Wright, et al., 1998, *Weed Science*, 46:24–29, "*In vitro* and whole–plant magnitude and cross–resistance characterization of two imidazolinone–resistant sugarbeet (*Beta vulgaris*) somatic cell selections".
Seefeldt, et al., 1998, *Weed Science*, 46:632–634, "Production of herbicide–resistant jointed goatgrass (*Aegilops cylindrica*) x wheat (*Triticum aestivum*) hybrids in the field by natural hybridization".
Harms, et al., 1992, *Mol. Gen. Genet.*, 233:427–435, "Herbicide resistance due to amplification of a mutant acetohydroxyacid synthase gene".
Lee, et al., 1988, *The Embro Journal*, 7:1241–1248, "The molecular basis of sulfonylurea herbicide resistance in tobacco".
Lovell, et al., 1996, *Weed Science*, 44:789–794, "Imidazolinone and sulfonylurea resistance in a biotype of common waterhemp (*Amaranthus rudis*)".
Foes, et al., 1999, *Weed Science*, 47:20–27, "A kochia (*Kochia scoparia*) biotype resistant to triazine and ALS–inhibiting herbicides".
Bing, D., 1991, M. Sc. Thesis, University of Saskatchewan, "Potential of gene transfer among oilseed brassica and their weedy relatives".
Newhouse, et al., 1988, *American Chemical Society Symposium Series Managing Resistance to Agrochemicals*, 421:474–482, "Genetic Modification of Crop Responses to Imidazolinone Herbicides".
Fehr, W.R., et al., 1987, *Mutation Breeding*, 1:286–303, "Principles of Cultivar Development".
Hattori, J., et al., 1995, *Mol Gen Genet*, 246: 419–425, "An Acetohydroxy acid synthase mutant reveals a single site involved in multiple herbicide resistance".
Hobbs, S.L.A., 1987, *Can. J. Plant Sci.*, 67: 457–466, "Comparison of Photosynthesis in Normal and Triazine–Resistant".

* cited by examiner

*Primary Examiner*—David H Kruse
(74) *Attorney, Agent, or Firm*—Pioneer Hi-Bred Int' l Inc.

(57) ABSTRACT

Improved varieties of *Brassica napus* having early maturity ("Early Napus") and resistance to an AHAS-inhibitor herbicide, such as an imidazolinone, are provided. These varieties may be used to produce inbreds or hybrids or to produce vegetable oil and meal. Parts of these plants, including plant cells, are also provided.

30 Claims, No Drawings

BRASSICA NAPUS WITH EARLY MATURITY (EARLY NAPUS) AND RESISTANCE TO AN AHAS-INHIBITOR HERBICIDE

CROSS-REFERENCE TO RELATED APPLICATIONS

This application claims priority under 35 USC 119(a) to Canadian Application No. 2,326,283 filed Nov. 17, 2000.

FIELD OF THE INVENTION

This invention is in the field of canola breeding. In particular, it relates to improved varieties of canola (*Brassica napus*) having early maturity ("Early Napus"), in combination with resistance to at least one AHAS-inhibitor herbicide.

BACKGROUND OF THE INVENTION

Canola is an important agricultural crop in Canada, the United States, Europe and Australia. Weed competition and earliness of maturity are significant limiting factors in canola crop production and quality. The challenge for plant scientists has been to develop canola varieties having superior performance with respect to these limiting factors, while at the same time having satisfactory agronomic characteristics, including yield potential, lodging resistance, oil and protein content, and glucosinolate levels that are sufficiently low for registration.

Resistance to AHAS-Inhibitor Herbicides

Herbicide resistant plants are plants that are able to survive and reproduce following exposure to herbicides at rates of application that would prevent non-herbicide resistant varieties of the same species from surviving and reproducing. Herbicide resistance is particularly important for *Brassica*, since many weeds, such as stinkweed, shepherd's purse, flixweed, ball mustard, wormseed mustard, hare's ear mustard and common peppergrass have a close genetic relationship with *Brassica*. Therefore, it is advantageous for a cultivar to have herbicide resistance not possessed by related weeds.

Some herbicides function by disrupting amino acid biosynthesis in affected species. For example, AHAS-inhibitor herbicides (also known as ALS-inhibitor herbicides) function by inhibiting the enzyme acetohydroxy acid synthase (AHAS), the first enzyme in the biosynthesis of the amino acids, isoleucine, leucine and valine. In plants with resistance to an AHAS-inhibitor herbicide, inhibition of the AHAS enzyme is prevented, thus allowing the plant to continue with normal amino acid biosynthesis. Most forms of *Brassica* are highly susceptible to AHAS-inhibitor herbicides, such as imidazolinones and sulfonylureas.

The development of canola with resistance to imidazolinones, such as PURSUIT™ and ODYSSEY™, was a major breakthrough in weed management technology. The imidazolinones are a family of broad spectrum herbicides which may be applied for in-crop weed control. They control a larger number of problem species than herbicides used in non-herbicide resistant varieties, and offer greater management flexibility, including timing of application and tank mixing. An advantage of imidazolinone ("IMI") resistant varieties over many other herbicide resistant varieties, such as ROUNDUP READY™ (glyphosate) or LIBERTY LINK™ (glufosinate) resistant varieties, is that some imidazolinone herbicides have a soil residual which controls successive weed flushes. This provides a significant advantage to farmers, because it enables them to achieve longer term weed control without a second application of herbicide. Effective weed control increases yield by reducing competition from weed species. It also improves grain quality through the elimination of cruciferous weed seeds. It may also improve weed management in other crops in the rotation, due to reduced weed pressure.

However, a drawback of currently available IMI resistant varieties is that they lack many of the desirable traits found in elite varieties of non-herbicide resistant canola. In particular, none of the currently available canola varieties have the desirable combination of IMI resistance and early maturity (Early Napus). It is particularly difficult to develop varieties having IMI resistance, in combination with other desirable traits, because the inheritance of the IMI resistance trait is relatively complex. Unlike the ROUNDUP READY™ trait or LIBERTY LINK™ trait, which are controlled by single transgenes that exhibit complete dominance, the IMI resistance trait is controlled by two unlinked gene pairs having partial dominance. Swanson et al., Plant Cell Reports 7:83–87 (1989) reported the development of imidazolinone herbicide tolerant *Brassica napus* mutants using microspore mutagenesis. During the process, five fertile double-haploid *Brassica napus* mutant plants were developed. One of the mutants was tolerant to between 5 and 10 times the recommended field traits of an imidazolinone herbicide. An inheritance study indicated that two semi-dominant unlinked genes combined to produce an F1 with greater tolerance than either of the parents.

Rutledge et al., Mol. Gen. Genet. 229:31–40 (1991) proposed a model for the inheritance of the five AHAS genes in *Brassica napus*. AHAS2, AHAS3 and AHAS4 appear to be associated with the 'A' (rapa) genome and AHAS1 and AHAS5 are likely associated with the 'C' (oleracea) genome. AHAS1 and AHAS3 are expressed at all growth stages (Ouellet et al., Plant J. 2:321–330 1992) and mutant forms of AHAS1 and AHAS3 appear to be the most effective tolerance genes. AHAS2 was found to be active only in ovules and seeds. AHAS4 was found to be defective due to interrupted sequences in the middle of the coding region (Rutledge et al., Mol. Gen Genet. 229:31–40 1991) and was not expressed in tissues examined by Ouellet et al., Plant J. 2:321–330 (1992). The last gene AHAS5, may also be defective (Rutledge et al. Mol. Gen Genet. 229:31–40, 1991). Hattori et al. Can J. Bot: 70:1957–1963, (1992) determined that the DNA sequence of the coding regions for AHAS1 and AHAS3 were 98% identical. DNA sequences of the 5' and the 3' ends were also closely related. Few similarities were observed between the sequence of the AHAS2 compared to the AHAS1 or AHAS3 genes.

There are two effective mutations for IMI resistance in commercial use—an AHAS1 mutant (believed to be located on the C genome) and an AHAS3 mutant (believed to be located on the A genome). The AHAS3 mutant also provides resistance to other AHAS-inhibitor herbicides, such as sulfonylureas. The complexity of the inheritance of the IMI resistance trait results in multiple phenotypes during segregating generations, which presents a significant hurdle to plant breeders. Accordingly, there is a need to develop an AHAS-inhibitor herbicide resistant canola variety with improved performance characteristics.

Early Napus

Early maturity is an important trait in *Brassica napus* varieties, especially in market areas with a limited frost-free period. Late summer frosts can damage the crop before it is fully mature, resulting in elevated green seed content of the grain (a grading criterion) and increased chlorophyll in the oil (a quality problem). High green seed results in losses to the producer, while elevated chlorophyll in the oil increases processing costs, and results in a loss of value for food end users. Early Napus is also important where early maturity reduces exposure to extreme heat and drought conditions during flowering and seed-filling.

To be classified as "Early Napus", a variety must have an average maturity which is at least four days earlier than the average maturity of the current WCC/RRC (Western Canadian Canola/Rapeseed Recommending Committee) check varieties (DEFENDER™, EXCEL™, and LEGACY™) over two years at 11 locations in the Short Season Zone of Western Canada. No known varieties of Brassica napus have the desirable combination of Early Napus and resistance to an AHAS-inhibitor herbicide, such as an imidazolinone. Therefore, there is a need for a Brassica napus variety which combines the advantageous traits of early maturity (Early Napus) and resistance to AHAS-inhibitor herbicides.

Accordingly, it is an object of the present invention to provide an improved variety of Brassica napus having early maturity (Early Napus) and resistance to at least one AHAS-inhibitor herbicide, such as an imidazolinone. These and other objects of the invention will be apparent to those skilled in the art from the following description and claims.

SUMMARY OF THE INVENTION

This invention provides a Brassica napus plant which is Early Napus and resistant to at least one AHAS-inhibitor herbicide, such as an imidazolinone (e.g. imazethapyr or imazamox) or a sulfonylurea [e.g. thifensulfuron methyl (REFINE™)]. In one embodiment, it relates to canola variety NS3801.

This invention also relates to tissue cultures of regenerable cells from the plants described above, as well as to the use of the tissue cultures for regenerating canola plants that are Early Napus and resistant to at least one AHAS-inhibitor herbicide, such as an imidazolinone or a sulfonylurea. It also relates to the plants produced therefrom.

This invention further relates to the parts of the Brassica napus plants described above, including their cells, pollen, ovules, roots, leaves, seeds, microspores and vegetative parts, whether mature or embryonic. It also relates to the use of these plant parts for regenerating a canola plant that is Early Napus and resistant to at least one AHAS-inhibitor herbicide, such as an imidazolinone or a sulfonylurea, and to the plants regenerated therefrom.

This invention further relates to the use of the plants described above for breeding a Brassica line, through pedigree breeding, crossing, self-pollination, haploidy, single seed descent, modified single seed descent, and backcrossing, or other suitable breeding methods, and to the plants produced therefrom. This invention also relates to a method for producing a first generation (F1) hybrid canola seed by crossing one of the plants described above with an inbred canola plant of a different variety or species, and harvesting the resultant first generation (F1) hybrid canola seed. It further relates to the plants produced from the F1 hybrid seed.

This invention also relates to the use of the Brassica napus plants described above for producing oil and/or meal, and to the vegetable oil and meal produced therefrom. Preferably, the plant is capable of producing oil with less than 2% erucic acid and meal with less than 30 µmol of glucosinolates per gram of defatted meal.

This invention provides substantial value to both producers and users of canola by providing hitherto unavailable combinations of early maturity (Early Napus) and resistance to at least one AHAS-inhibitor herbicide. This trait combination improves weed control, while improving or stabilizing grain quality by reducing green seed count.

DETAILED DESCRIPTION OF THE INVENTION

In accordance with this invention, improved varieties of Brassica napus having early maturity (Early Napus) and resistance to at least one AHAS-inhibitor herbicide are developed by crossing a parent with resistance to an AHAS-inhibitor herbicide with one or more parents having early maturity (Early Napus), wherein the herbicide resistant parent and the Early Napus parent(s) together have the genetic basis for the complement of characteristics desired in the progeny. Self-pollination or sib-mating following crossing leads to a segregation of traits among the progeny. Progeny having the desired combination of traits are selected after exposure to one or more appropriate AHAS-inhibitor herbicides and evaluation for desirable traits over successive generations.

Various breeding methods may be used, including haploidy, pedigree breeding, single-seed descent, modified single seed descent, recurrent selection, and backcrossing. Because of the complex inheritance of the AHAS-inhibitor herbicide resistant trait, we have found that haploidy is the most effective breeding method. Parents having the desired complement of characteristics are crossed in a simple or complex cross. Crossing (or cross-pollination) refers to the transfer of pollen from one plant to a different plant. Progeny of the cross are grown and microspores (immature pollen grains) are separated and filtered, using techniques known to those skilled in the art [(e.g. Swanson, E. B. et al., Plant Cell Reports, "Efficient isolation of microspores and the production of microspore-derived embryos in Brassica napus", 6:94–97 (1987); and Swanson, E. B., Microspore Culture in Brassica, pp. 159–169 in: Methods in Molecular Biology, Vol. 6, Plant Cell and Tissue Culture, Humana Press (1990)]. These microspores exhibit segregation of genes. The microspores are cultured in the presence of an appropriate AHAS-inhibitor herbicide, such as imazethapyr (e.g. PURSUIT™) or imazamox (e.g. RAPTOR™) or a 50/50 mix of imazethapyr and imazamox (e.g. ODYSSEY™), which kills microspores lacking the mutations responsible for resistance to the herbicide. Microspores carrying the mutant genes responsible for resistance to the herbicide survive and produce embryos, which form haploid plants. Their chromosomes are then doubled to produce doubled haploids.

The doubled haploids are evaluated in subsequent generations for herbicide resistance, early maturity, and other desirable traits. AHAS-inhibitor herbicide resistance may be evaluated by exposing plants to one or more appropriate AHAS-inhibitor herbicides and evaluating herbicide injury. Earliness of maturity can be evaluated through visual inspection of seeds within pods (siliques) on the plants. Some other traits, such as lodging resistance and plant height may also be evaluated through visual inspection of the plants. Blackleg resistance may be evaluated by inoculating plants with blackleg spores to induce the disease, and observing resistance to infection. Other traits, such as oil percentage, protein percentage, and total glucosinolates of the seeds may be evaluated using techniques such as Near Infrared Spectroscopy.

It is also possible to analyze the genotype of the plants, using techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as "Microsatellites".

Evaluation and manipulation (through exposure to one or more appropriate AHAS-inhibitor herbicides, and blackleg infection) typically occurs over several generations. The performance of the new lines is evaluated using objective criteria in comparison to check varieties. Lines showing the desired combination of traits are self-pollinated to produce seed. Self-pollination refers to the transfer of pollen from one flower to the same flower or another flower of the same plant. Plants that have been self-pollinated and selected for type for many generations become homozygous at almost all gene loci and produce a uniform population of true breeding progeny.

Other breeding methods may also be used. For example, pedigree breeding is commonly used for the improvement of largely self-pollinating crops such as canola. Pedigree breeding starts with the crossing of two genotypes, each of which may have one or more desirable characteristics that is lacking in the other or which complements the other. If the two original parents do not provide all of the desired characteristics, additional parents can be included in the crossing scheme.

These parents are crossed in a simple or complex manner to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best families, and the best individuals within the best families are selected. Replicated testing of families (lines) can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars.

The single seed descent (SSD) procedure may also be used to breed improved varieties. The SSD procedure in the strict sense refers to planting a segregating population, harvesting a sample of one seed per plant, and using the population of single seeds to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the plants originally sampled in the $F_2$ population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Backcross breeding can be used to transfer a gene or genes for a simply inherited, highly heritable trait from one line or cultivar (the donor parent) into another desirable cultivar or inbred line (the recurrent parent). After the initial cross, individuals possessing the phenotype of the donor parent are selected and are repeatedly crossed (backcrossed) to the recurrent parent. When backcrossing is complete, the resulting plant is expected to have the attributes of the recurrent parent and the desirable trait transferred from the donor parent.

Improved varieties may also be developed through recurrent selection. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Regeneration of Plants

This invention also relates to the parts of the plants disclosed herein, including plant cells, tissue, pollen, ovules, roots, leaves, seeds, and microspores, whether mature or embryonic.

The plants produced in accordance with the present invention may be regenerated from plant parts using known techniques. For instance, seeds from the plants of the present invention may be planted in accordance with conventional *Brassica* growing procedures. These plants will generate further seeds following self-pollination. Alternatively, doubled haploid plantlets may be extracted to immediately form homozygous plants, using known procedures.

*Brassica* plants may also be regenerated using tissue culture and regeneration. Tissue culture of various tissues of canola and regeneration of plants therefrom is known to those skilled in the art. For example, the propagation of a canola cultivar by tissue culture is described in the following references: Chuong et al., "A Simple Culture Method for *Brassica* Hypocotyl Protoplasts", Plant Cell Reports 4:4–6 (1985); Barsby, T. L. et al. "A Rapid and Efficient Alternative Procedure for the Regeneration of Plants from Hypocotyls Protoplasts of *Brassica napus*", Plant Cell Reports, (Spring 1996); Kartha, K. et al. "In vitro Plant Formation from Stem Explants of Rape" Physiol. Plant, 31:217–220 (1974); Narashimhulu, S. et al., "Species Specific Shoot Regeneration Response of Cotyledenary Explants of *Brassicas*", Plant Cell Reports, (Spring 1988); Swanson, E., "Microspore Culture in Brassica", Methods of Molecular Biology, Vol. 6, Chapter 17, p.159 (1990).

Use of *Brassica* as a Breeding Line

The *Brassica napus* plants of this invention may be used to breed a novel *Brassica* line. The combination of desired traits described herein, once established, can be transferred into other *Brassica napus* plants by known plant breeding techniques including self-pollination, crossing, recurrent selection, backcross breeding, pedigree breeding, single seed descent, modified single seed descent, haploidy, and other suitable breeding methods.

The desired traits can also be transferred between *Brassica* species, such as *B. napus, B. rapa* (formerly known as *B. campestris*), and *B. juncea*, using the same known plant breeding techniques involving pollen transfer and selection. The transfer of traits between *Brassica* species, such as *napus* and *rapa* by known plant breeding techniques is well documented in the technical literature (see for instance, Tsunada et al., 1980, *Brassica* Crops and Wild Alleles Biology and Breeding", Japan Scientific Press, Tokyo).

As an example of the transfer of the desired traits described herein from *napus* to *rapa*, one selects a commercially available *rapa* variety such as REWARD™, GOLDRUSH™, and KLONDIKE™, and carries out an interspecific cross with one of the plants from the present invention. After the interspecific cross, members of the F1 generation are self-pollinated to produce $F_2$ oilseed. Selection for the desired traits is then conducted on single $F_2$ plants which are then backcrossed with the *rapa* parent through the number of generations required to obtain a euploid (n=10) *rapa* line exhibiting the desired combination of traits.

In order to avoid inbreeding depression (e.g. loss of vigour and fertility) that may accompany the inbreeding of *Brassica rapa*, selected, i.e. $BC_1$ plants that exhibit similar desired traits while under genetic control advantageously can be sib-mated. The resulting oilseed from these crosses can be designated $BC_1SIB_1$ oilseed. Accordingly, the fixation of the desired alleles can be achieved in a manner analogous to self-pollination while simultaneously minimizing the fixation of other alleles that potentially exhibit a negative influence on vigor and fertility.

This invention is also directed to methods for producing an F1 hybrid seed by crossing a first parent *Brassica napus* plant with a second parent *Brassica* plant, wherein the first parent plant is an inbred *Brassica napus* plant, such as canola variety NS3801, which is Early Napus and resistant to at least one AHAS-inhibitor herbicide. This invention is also related to the plants produced from the F1 hybrid seed and the cells and other parts of those plants.

Alternatively, both first and second parent *Brassica* plants can come from the same varieties. Advantageously, one of the *Brassica* varieties of the present invention is used in crosses with a different *Brassica* inbred to produce first generation ($F_1$) canola hybrid seeds and plants with superior characteristics and increased vigour.

Preferably when generating hybrid plants, the parent should have glucosinolate levels that are sufficiently low to ensure that the seed of the $F_1$ hybrid has glucosinolate levels within regulatory levels. The glucosinolate level of the seed harvested from the $F_1$ hybrid is roughly the average of the glucosinolate levels of the male and female parents. For example, if the objective is to obtain hybrid grain ($F_2$) having a glucosinolate level of less than 20 $\mu$mol/g, and one parent has a glucosinolate level of 15 $\mu$mol/g, the other parent must have a glucosinolate level of 25 $\mu$mol/g or less.

Vegetable Oil and Meal

The seed of the plants of this invention may be used for producing vegetable oil and meal. The seed of these varieties, the plant produced from such seed, the hybrid canola plant produced from the crossing of these varieties with other inbred varieties, the resulting hybrid seed, and various parts of the hybrid canola plant can be utilized in the production of an edible vegetable oil or other food products in accordance with known techniques. The remaining solid meal component derived from seeds can be used as a nutritious livestock feed. Canola variety NS3801 can be used to produce oil of improved quality, due to lower chlorophyll levels in the oil. Preferably, the oil has less than 2% erucic acid and the meal has less than 30 $\mu$mol of glucosinolates per gram of defatted meal.

A preferred embodiment of this invention is set forth below. It should be understood, however, that the invention is not limited to the specific details set forth in this example.

Development of the Improved IMI Resistant *Brassica napus* Line, NS3801.

| | |
|---|---|
| Generation: | Parent to F1 |
| Seed Planted: | BULLET ™ and DEFENDER ™, two spring canola varieties developed by Svalof-Weibulls, and marketed commercially by Proven Seed |
| Seed Harvested: | 94SN-9514 = (BULLET ™/DEFENDER ™) |
| Method: | Parents were grown and crossing was carried out in a controlled environment in the greenhouse. |
| Generation: | Single cross F1 to three-way cross F1 |
| Seed Planted: | 94SN-9514 = (BULLET ™ × DEFENDER ™) and 45A71 (Breeder code NS1471, registered imidazolinone resistant spring canola variety from Pioneer Hi-Bred, commercially available from Proven Seed) |
| Seed Harvested: | 96SN-0564 = (45A71 × (BULLET ™ × DEFENDER ™)) |
| Method: | Parents were grown and crossing was carried out in a controlled environment in the greenhouse. 45A71 was used as the female parent. Approximately six female plants and more than 10 male plants were sampled in making the three-way cross. IMI resistance was contributed by 45A71, which is homozygous for the imidazolinone resistant genes. |
| Generation: | Three way Cross F1 to doubled haploid (F-infinity) |
| Seed Planted: | 96SN-0564 = (45A71 × (BULLET ™ × DEFENDER ™)) |
| Seed Harvested: | 97DHS-6259 |
| Method: | Twelve plants of 96SN-0564 were planted in the growth room under controlled environment as donor plants. These plants were sprayed with the herbicide, PURSUIT ™ (imazethapyr), at 1x level. Immature buds were harvested from each donor plant and were crushed in a blender to produce a slurry [as described in Swanson, E. B. et al., "Efficient isolation of microspores and the production of microspore-derived embryos in *Brassica napus*" L. Plant Cell Reports 6:94–97 (1987); and Swanson, E. B. Microspore culture in Brassica, pgs. 159–169 in: Methods in Molecular Biology vol. 6, Plant Cell and Tissue Culture, Humana Press (1990)]. The slurry was then filtered through two layers of Nitex filters (48 $\mu$m pores) and collected in centrifuge tubes. The suspensions were centrifuged, decanted and washed three times for a total of 4 spins. Microspores were counted using a haemocytometer and plated in NLN medium [Lichter, R., "Induction of haploid plants from isolated pollen of *Brassica napus*, Z. Pflanzenphysiol. Bd. 105:427–434, (1982)], containing 40 $\mu$g/l PURSUIT ™, at a density of 60,000 microspores per ml. Ten ml of this suspension were poured into 100 × 25 mm petri plates wrapped with parafilm, and placed in a Percival incubation chamber at 32.5° C. in darkness for 15 days. During this period the microspores carrying imidazolinone-resistant genes were expected to survive and produce embryos. After 15 days, petri plates with cotyledonary embryos were put in a rotary shaker for 6 to 13 days before being transferred to a solid 0.8% agar medium with 0.1% Gibberillic acid (GA) in petri plates. Transferred embryos were incubated in the dark at 4–8° C. for 7–10 days and removed to a Percival incubation chamber in light at 20 to 25° C. for 3 to 5 weeks. Selected embryos that regenerated were placed in soil in 72 cell flats or put back onto 0.8% agar with 0.1% GA for a further 3 to 5 weeks before they were transplanted into the soil. Before flowering, plants were treated with 0.33% colchicine for 1.5 to 2.5 hours. Plant roots were washed free of soil prior to incubation in the colchicine solution. After treatment they were planted in 10 cm plastic pots. Upon flowering, plants with fertile (diploid) racemes were covered with perforated, clear plastic bags to produce selfed seeds. After flowering, bags were removed and plants were dried down, seed was harvested, cleaned and cataloged with a DHS number. Lines with 100 seeds or more were prepared for nursery evaluation. |

-continued

| | |
|---|---|
| Generation: | Doubled haploid evaluation |
| Seed Planted: | 97DHS-6259 along with the check varieties 46A72 (NS1472), 45A71 (NS1471) and 46A74 (NS2211) |
| Seed Harvested: | In order to perform quality analysis, twenty grams of open pollinated seed was harvested from 97DHS-6259. An equal amount of seed was harvested from the check rows. After completing the evaluation and finalizing selections, seed was harvested from the entire row for each selected line including 97DHS-6259. |
| Method: | Several hundred imidazolinone resistant spring canola doubled haploid lines, including 97DHS-6259, were planted in the breeding nursery (project X823A) for evaluation purpose. Each line was planted in a three meter long row with approximately 100 seeds/row. 46A72 was planted in every 20th row (#1, 20, 40, 60 etc.) for use as a quality check. 45A71 and 46A74, commercial imidazolinone resistant varieties from Pioneer Hi-Bred, were planted as checks in rows, 10, 50, 90 and 30, 70 110 of each range. The entire nursery was sprayed with ODYSSEY ™ (a 50/50 mix of imazethapyr and imazamox) at 30 g/ha when plants were at the 4-leaf stage. A second application of ODYSSEY ™ (30 g/h) was made when plants were in the rosette stage. Doubled haploid lines showing herbicide injury were noted. Observations recorded included: days to flowering, days to maturity, agronomic score at flowering and agronomic score at maturity. At physiological maturity, lines to be harvested were selected visually. A 20 g seed sample was harvested from each of the selected lines. The quality check rows of 46A72 were also harvested. The samples were analyzed in the lab and for oil percentage, protein percentage, and total glucosinolates using NIR (Near Infrared Spectroscopy). Final selection of lines was based on days to maturity, agronomic score at maturity, oil percentage, protein percentage and total glucosinolates. Several doubled haploid lines were selected including 97DHS-6259. |
| Generation: | Greenhouse Pure seed increase |
| Seed Planted: | 97DHS-6259 |
| Seed Harvested: | 97DHS-6259 |
| Method: | Each selected line including 97DHS-6259, was planted in the greenhouse (project SN-707) using remnant pure seed. All lines were sprayed with 60 g/ha ODYSSEY ™ (2x rate) at the 4-leaf stage, in order to confirm imidazolinone resistance. All lines were inoculated with blackleg (*Phoma lingam*) spores, to induce disease development. Lines showing herbicide injury and/or susceptibility to blackleg were discarded. Selected lines, including 97SS-6259 were self-pollinated to produce 20 g of seed, and were assigned new code numbers. 97SN-6259 was assigned the code, NS3801. |
| Generation: | Field Evaluation (R200 tests) |
| Seed Planted: | NS3801 |
| Seed Harvested: | NS3801 |
| Method: | The selected lines including NS3801, were evaluated in a two replicate yield trial (R221) planted at six locations in western Canada. Plot size was 9 square meters (6 m x 1.5 m). The seeding rate was 5.5 kg/ha. Appropriate check varieties were included in the yield trial. The same entries were planted in a disease trail where blackleg inoculum was applied to ensure uniform disease infection. Observations recorded included: days to flowering, days to maturity, lodging score (1 = poor, 9 = good), yield (q/ha), and moisture percentage. At harvest, a 15 gram seed sample was collected from each plot, and was analyzed to determine oil percentage, protein percentage, total glucosinolates, and fatty acid composition. |

Table 1 illustrates the performance of *Brassica napus* variety NS3801 in comparison to WCC/RRC check varieties.

| VARIETY | Yield** (Qu/Ha) | Yield (% Chk) | Maturity (Days) | Oil (%) | Protein (%) | Glucs (uM/g) | Blackleg (1–9)** |
|---|---|---|---|---|---|---|---|
| NS3801 | 29.60 | 93.36 | 102.40 | 48.29 | 46.30 | 13.89 | 8.44 |
| Defender | 29.67 | 93.80 | 105.70 | 48.16 | 48.14 | 13.63 | 6.57 |
| Excel | 33.93 | 107.27 | 109.50 | 49.70 | 47.67 | 18.08 | 6.04 |
| Legacy | 31.34 | 99.08 | 108.40 | 49.64 | 48.75 | 10.90 | 5.57 |
| Mean of Napus Chks # | 31.65 | 100.05 | 107.87 | 49.17 | 48.19 | 14.20 | 6.06 |
| Difference | -2.05 | -6.69 | -5.47 | -0.88 | -1.89 | -0.31 | 2.38 |

*Data from Pioneer Hi-Bred Trials in the Short Season Zone of Western Canada
**Trait Definitions: Yield = seed yield in quintals (decitonnes) per hectare and as percentage of Checks Mean; Maturity = days from Planting to physiological maturity; Oil & Protein as percentage of total seed weight at 8.5% moisture; Glucs = aliphatic glucosinolates in seed at 8.5% moisture, expressed in micromoles per gram
WCC/RRC Check Varieties for B. napus & B. rapa. For registration of early B. napus varieties, yield and composition are Compared to B. rapa, and maturity is compared to B. napus, where Early Napus = -4 days or more vs. B. napus checks

Deposits

This invention is not to be construed as limited to the particular embodiments disclosed, since these are regarded as illustrative rather than restrictive. Moreover, variations and changes may be made by those skilled in the art without departing from the spirit of this invention.

The seeds of the subject invention were deposited in the American Type Culture Collection (ATCC), 10801 University Blvd., Manassas, Va. 20110-2209, USA:

| Seed | Accession Number | Deposit Date |
| --- | --- | --- |
| Brassica napus NS3801 | PTA-2470 | Sep. 14, 2000 |

The deposit will be maintained at ATCC, P.O. Box 1549, Manassas, Va. 201008. Access to this deposit will be available during the pendancy of the application to the Commissioner of Patents and Trademarks and persons determined by the Commissioner to be entitled thereto upon request. This deposit will be maintained under the terms of the Budapest Treaty on the International Recognition of the Deposit of Microorganisms for the Purposes of Patent Procedure. The deposit will irrevocably and without restriction or condition be available to the public upon issuance of a patent. However, it should be understood that the availability of a deposit does not constitute a license to practice the subject invention in derogation of patent rights granted by government action or under the Plant Variety Protection Act (7 USC 2321 et seq.).

What is claimed is:

1. A plant cell of a *Brassica napus* plant which is Early Napus and resistant to at least one AHAS-inhibitor herbicide, wherein said plant is variety NS3801, representative seed of said variety having been deposited under ATCC Accession No. PTA-2470.

2. The plant cell of claim 1, wherein said AHAS-inhibitor herbicide is an imidazolinone.

3. The plant cell of claim 2, wherein said imidazolinone is imazethapyr or imazamox or a combination thereof.

4. The plant cell of claim 1, wherein said AHAS-inhibitor herbicide is a sulfonylurea.

5. The plant cell of claim 4, wherein said sulfonylures is thifensulfuron methyl.

6. A tissue culture of regenerable cells of a *Brassica napus* plant which is Early Napus and resistant to at least one AHAS-inhibitor herbicide, wherein said plant is variety NS3801, representative seed of said variety having been deposited under ATCC Accession No. PTA-2470.

7. The tissue culture of claim 6, wherein said AHAS-inhibitor herbicide is an imidazolinone.

8. The tissue culture of claim 7, wherein said imidazolinone is imazethapyr or imazamox or a combination thereof.

9. The tissue culture of claim 6, wherein said AHAS-inhibitor herbicide is a sulfonylurea.

10. The tissue culture of claim 9, wherein said sulfonylurea is thifensulfuron methyl.

11. A *Brassica napus* plant or plant part which is Early Napus and resistant to at least one AHAS-inhibitor herbicide, wherein said plant is variety NS3801, representative seed of said variety having been deposited under ATCC Accession No. PTA-2470.

12. The plant part of claim 11, wherein said plant part is selected from a group consisting of a tissue, pollen, ovule, root, leaf, seed and microspore.

13. The plant part of claim 11, wherein said AHAS-inhibitor herbicide is an imidazolinone.

14. The plant part of claim 13, wherein said imidazolinone is imazethapyr or imazamox or a combination thereof.

15. The plant part of claim 11, wherein said AHAS-inhibitor herbicide is a sulfonylurea.

16. The plant part of claim 15, wherein said sulfonylurea is thifensulfuron methyl.

17. A method for regenerating a *Brassica napus* plant which is Early Napus and resistant to at least one AHAS-inhibitor herbicide, the method comprising growing the plant part of claim 11 under conditions sufficient to produce a regenerated plant.

18. A method for breeding a *Brassica* line comprising crossing a first *Brassica* plant which is Early Napus and resistant to at least one AHAS-inhibitor herbicide with a second *Brassica* plant different from said first plant, wherein said first *Brassica* plant is variety NS3801, representative seed of said variety having been deposited under ATCC Accession No. PTA-2470.

19. The method in accordance with claim 18, wherein said AHAS-inhibitor herbicide is an imidazolinone.

20. The method in accordance with claim 19, wherein said imidazolinone is imazethapyr or imazamox or a combination thereof.

21. The method in accordance with claim 18, wherein said AHAS-inhibitor herbicide is a sulfonylurea.

22. The method in accordance with claim 21, wherein said sulfonylurea is thifensulfuron methyl.

23. A method for producing a first generation (F1) hybrid seed comprising crossing a first *Brassica napus* plant that is Early Napus and resistant to at least one AHAS-inhibitor herbicide with a second *Brassica napus* plant different from said first plant and harvesting the resultant first generation (F1) hybrid seed, wherein said first plant is variety NS3801, representative seed of said variety having been deposited under ATCC Accession No. PTA-2470.

24. The method in accordance with claim 23, wherein said AHAS-inhibitor herbicide is an imidazolinone.

25. The method in accordance with claim 24, wherein said imidazolinone as imazethapyr or imazamox or a combination thereof.

26. The method in accordance with claim 23, wherein said AHAS-inhibitor herbicide is a sulfonylurea.

27. The method in accordance with claim 26, wherein said sulfonylurea is thifensulfuron methyl.

28. A *Brassica napus* F1 progeny plant or plant part produced from variety NS3801, wherein said progeny plant or plant part is Early Napus and resistant to at least one AHAS-inhibitor herbicide, representative seed of said variety having been deposited under ATCC Accession No. PTA-2470.

29. A *Brassica napus* F1 progeny plant seed produced from variety NS3801, wherein said progeny plant seed is Early Napus and resistant to at least one AHAS-inhibitor herbicide, representative seed of said variety having been deposited under ATCC Accession No. PTA-2470.

30. A *Brassica napus* F1 progeny plant cell produced form variety NS3801, wherein said progeny plant cell is Early Napus and resistant to at least one AHAS-inhibitor herbicide, representative seed of said variety having been deposited under ATCC Accession No. PTA-2470.

* * * * *

UNITED STATES PATENT AND TRADEMARK OFFICE
CERTIFICATE OF CORRECTION

PATENT NO. : 6,914,171 B2
DATED : July 5, 2005
INVENTOR(S) : David G. Charne et al.

It is certified that error appears in the above-identified patent and that said Letters Patent is hereby corrected as shown below:

Column 11,
Lines 43-44, should read as follows:
-- The plant cell of claim 4, wherein said sulfonlyurea is thifensulfuron methyl. --.

Column 12,
Lines 60-64, should read as follows:
-- A Brassica napus F1 progeny plant cell produced from variety NS3801, wherein said progeny plant cell is Early Napus and resistant to at least one AHAS-inhibitor herbicide, representative seed of said variety having been deposited under ATCC Accession No. PTA-2470. --.

Signed and Sealed this

Thirtieth Day of August, 2005

JON W. DUDAS
*Director of the United States Patent and Trademark Office*